United States Patent
Oron et al.

(10) Patent No.: US 9,403,030 B2
(45) Date of Patent: Aug. 2, 2016

(54) LOW LEVEL LASER THERAPY FOR ALZHEIMER'S DISEASE

(75) Inventors: Uri Oron, Rishon Lezion (IL); Hana Tuby, Bney Brak (IL); Dan Frenkel, Rehovot (IL); Dorit Farfara, Rehovot (IL)

(73) Assignee: RAMOT AT TEL-AVIV UNIVERSITY LTD., Tel Aviv (IL)

(*) Notice: Subject to any disclaimer, the term of this patent is extended or adjusted under 35 U.S.C. 154(b) by 424 days.

(21) Appl. No.: 14/005,561

(22) PCT Filed: Mar. 25, 2012

(86) PCT No.: PCT/IB2012/051414
§ 371 (c)(1),
(2), (4) Date: Oct. 23, 2013

(87) PCT Pub. No.: WO2012/131558
PCT Pub. Date: Oct. 4, 2012

(65) Prior Publication Data
US 2014/0039581 A1   Feb. 6, 2014

Related U.S. Application Data

(60) Provisional application No. 61/468,017, filed on Mar. 27, 2011.

(51) Int. Cl.
*A61N 5/06* (2006.01)
*A61N 5/00* (2006.01)
*A61N 5/067* (2006.01)

(52) U.S. Cl.
CPC ............. *A61N 5/0618* (2013.01); *A61N 5/0603* (2013.01); *A61N 2005/005* (2013.01); *A61N 2005/063* (2013.01); *A61N 2005/067* (2013.01); *A61N 2005/0612* (2013.01); *A61N 2005/0645* (2013.01); *A61N 2005/0651* (2013.01); *A61N 2005/0659* (2013.01); *A61N 2005/0662* (2013.01)

(58) Field of Classification Search
None
See application file for complete search history.

(56) References Cited

U.S. PATENT DOCUMENTS

| | | | |
|---|---|---|---|
| 5,149,955 A | 9/1992 | Kitamura et al. | |
| 5,733,541 A | 3/1998 | Taichman et al. | |
| 6,312,451 B1 | 11/2001 | Streeter | |
| 6,358,272 B1 * | 3/2002 | Wilden | A61C 17/00 606/13 |
| 6,395,016 B1 | 5/2002 | Oron et al. | |
| 6,602,274 B1 | 8/2003 | Chen | |

(Continued)

OTHER PUBLICATIONS

Yang X, Askarova S, Sheng W, Chen JK, Sun AY, Sun GY, Yao G, Lee JC. Low energy laser light (632.8 nm) suppresses amyloid-β peptide-induced oxidative and inflammatory responses in astrocytes. Neuroscience. Dec. 15, 2010;171(3):859-68.*

(Continued)

*Primary Examiner* — Brian T Gedeon
*Assistant Examiner* — Ankit D Tejani
(74) *Attorney, Agent, or Firm* — D. Kligler IP Services Ltd.

(57) ABSTRACT

Methods and systems are provided for delivering visible or infrared biostimulatory energy to bone marrow to subjects having or developing Alzheimer's disease. The radiation is delivered to sites remote from the brain at a dose sufficient to cause stimulated mesenchymal stem cells to appear in the brain and degrade β-amyloid. The energy may be coherent light and can be administered transcutaneously, subcutaneously, or via an intramedullary probe.

29 Claims, 5 Drawing Sheets

(56) References Cited

U.S. PATENT DOCUMENTS

| | | | |
|---|---|---|---|
| 6,676,655 | B2 | 1/2004 | McDaniel |
| 6,849,051 | B2 | 2/2005 | Sramek et al. |
| 6,866,678 | B2 | 3/2005 | Shenderova et al. |
| 6,899,723 | B2 | 5/2005 | Chen |
| 7,309,438 | B2 | 12/2007 | Filbert |
| 2003/0125782 | A1 | 7/2003 | Streeter |
| 2006/0212100 | A1* | 9/2006 | Wu ............... A61N 5/0619 607/93 |
| 2007/0135874 | A1 | 6/2007 | Bala |
| 2009/0060886 | A1 | 3/2009 | Alt |
| 2009/0131827 | A1* | 5/2009 | Crocker ........... A61B 10/025 600/571 |
| 2009/0254154 | A1* | 10/2009 | De Taboada ....... A61N 5/0613 607/88 |
| 2010/0053391 | A1 | 3/2010 | Huang |
| 2010/0094384 | A1* | 4/2010 | De Taboada ....... A61N 5/0613 607/88 |
| 2010/0105977 | A1* | 4/2010 | De Taboada ....... A61N 5/0613 600/9 |
| 2011/0060266 | A1 | 3/2011 | Streeter et al. |
| 2012/0041521 | A1 | 2/2012 | Oron et al. |

OTHER PUBLICATIONS

International Application PCT/IB2010/052133 Search Report dated Nov. 26, 2010.
Morgan, D., "Amyloid, memory and neurogenesis", Experimental Neurology, vol. 205, issue 2, pp. 330-335, Jun. 2007.
Selkoe, D.J., "Cell biology of protein misfolding; the examples of Alzheimer's and Parkinson's diseases", Nature Cell Biology, vol. 6, No. 11, pp. 1054-1061, Nov. 2004.
Liechty et al., "Human mesenchymal stem cells engraft and demonstrate site-specific differentiation after in utero transplantation in sheep", Nature Medicine, vol. 6, No. 11, pp. 1282-1286, Nov. 2000.
Simard et al., "Bone Marrow-Derived microglia play a critical role in restricting plaque formation in Alzheimer's disease", Neuron 49, pp. 489-502, Feb. 16, 2006.
Shefer et al., "Low-energy laser irradiation promotes the survival and cell cycle of skeletal muscle satellite cells", Journal of Cell Science, vol. 115, pp. 1461-1469, Jan. 8, 2002.
Oakley et al., "Intraneuronal b-Amyloid aggregates, neurodegeneration, and neuron loss in transgenic mine with five familial Alzheimer's disease mutations: potential factors in Amyloid plaque formation", The Journal of Neuroscience, vol. 26, No. 40, pp. 10129-10140, Oct. 4, 2006.
Boheler et al., "Differentiation of pluripotent embryonic stem cells into cardiomyocytes", Circulation Research, Journal of the American Heart Association, vol. 91, pp. 189-201, Aug. 9, 2002.
Orlic et al., "BM cells regenerate infarcted Myocardium", Nature, vol. 410, pp. 701-704, Apr. 1, 2005.
Jiang et al., "Homing and differentiation of mesenchymal stem cells delivered intravenously to ischemic myocardium in vivo: a time-series study", Pflügers Archiv—European Journal of Physiology, vol. 453, No. 1, pp. 43-52, Aug. 17, 2006.
Yaakobi et al., "Long-term effect of low energy laser irradiation on infarction and reperfusion injury in the rat heart", Journal of Applied Physiology, vol. 90, pp. 2411-2419, Jan. 30, 2001.
Davani et al., "Mesenchymal progenitor cells differentiate into an endothelial phenotype, enhance vascular density, and improve heart function in a rat cellular cardiomyoplasty model", Circulation, vol. 108:II, pp. 253-258, Sep. 9, 2003.
Simard et al., "Bone marrow stem cells have the ability to populate the entire central nervous system into fully differentiated parenchymal microglia", The FASEB Journal, vol. 18, pp. 998-1000, Jun. 2004.
Uccelli et al., "Mesenchymal stem cells in health and disease", Nature Reviews/Immunology, vol. 8, pp. 726-736, Sep. 2008.
Devine et al., "Mesenchymal stem cells are capable of homing to the bonemarrow of non-human primates following systemic infusion", Experimental Hematology, vol. 29, issue 2, pp. 244-255, Feb. 2001.
Conlan et al., "Biostimulation of wound healing by low-energy laser irradiation: A review", Journal of Clinical Periodontology, vol. 23, issue 5, pp. 492-496, May 1996.
Lee et al., "Bonemarrow-derivedmesenchymalstemcellsreducebrain amyloid-β deposition and accelerate the activation of microglia in an acutely induced Alzheimer's disease mouse model", Neuroscience Letters, vol. 450, issue 2, pp. 136-141, Jan. 30, 2009.
Bibikova et al., "Promotion of muscle regeneration in the toad (*Bufo viridis*) gastrocnemius muscle by low-energy laser irradiation", The Anatomical Record, vol. 235, issue 3, pp. 374-380, Mar. 1993.
Bibikova et al., "Enhancement of angiogenesis in regenerating gastrocnemius muscle of the toad (*Bufo viridis*) by low-energy laser irradiation", Anatomy and Embryology, vol. 190, No. 6, pp. 597-602, year 1994.
Shefer et al., "Skeletal muscle cell activation by low-energy laser irradiation: A role for the MAPK/ERK pathway", Journal of Cellular Physiology, vol. 187, issue 1, pp. 73-80, Apr. 2001.
Oron et al., "Attenuation of the formation of scar tissue in rats and dogs post myocardial infarction by low energy laser irradiation", Lasers in Surgery and Medicine, vol. 28, pp. 204-211, year 2001.
Oron et al., "Low energy laser irradiation reduces formation of scar tissue following myocardial infarction in rats and dogs", Circulation, vol. 102, pp. 296-301, year 2001.
Tuby et al., "Modulations of VEGF and iNOS in the rat heart by low level laser therapy are associated with cardioprotection and enhanced angiogenesis", Lasers in Surgery and Medicine, vol. 38, issue 7, pp. 682-688, Aug. 2006.
Oron et al., "Ga-As (808 nm) Laser Irradiation Enhances ATP Production in Human Neuronal Cells in Culture", Photomedicine and Laser Surgery, vol. 25, No. 3, pp. 180-182, Jun. 2007.
De Souza et al., "Low power laser radiation at 685 nm stimulates stem-cell proliferation rate in Dugesia tigrina during regeneration", Journal of Photochemistry and Photobiology B: Biology, vol. 80, issue 3, pp. 203-207, Sep. 1, 2005.
Tuby et al., "Implantation of low-level laser irradiated mesenchymal stem cells into the infarcted rat heart is associated with reduction in infarct size and enhanced angiogenesis", Photomedicine and Laser Surgery, vol. 27, No. 2, pp. 227-234, year 2008.
Farfara et al., "γ-Secretase Component Presenilin is Important for Microglia b-Amyloid Clearance", Annals of Neurology, vol. 69, issue 1, pp. 170-180, Nov. 22, 2010.
International Application PCT/IB2012/051414 filed on Mar. 25, 2012.
International Application PCT/IB2012/051414 Search report dated Jun. 27, 2012.
Bittira et al., "Mobilization and homing of bone marrow stromal cells in myocardial infarction", European Journal Cardio-Thoracic Surgery, vol. 24, No. 3, pp. 393-398, Sep. 2003.
Wang et al., "Combining pharmacological mobilization with intramyocardial delivery of bone marrow cells over-expressing VEGF is more effective for cardiac repair", Journal of Molecular and Cellular Cardiology, vol. 40, issue 5, pp. 736-745, May 2006.
Karu, T., "Primary and secondary mechanisms of action of visible to near-IR radiation on cells", Journal of Photochemistry and Photobiology B: Biology; vol. 49, issue 1, pp. 1-17, Mar. 1999.
Yu et al., "Photomodulation of Oxidative Metabolism and Electron Chain Enzymes in Rat Liver Mitochondria", Photochemistry and Photobiology, vol. 66, issue 6, pp. 866-871, Dec. 1997.
Oron, U., "Photoengineering of tissue repair in skeletal and cardiac muscles—Review", Photomedicine and Laser Surgery, vol. 24, pp. 111-120, year 2006.
Tuby et al., "Low-level laser irradiation (LLLI) promotes proliferation of mesenchymal and cardiac stem cells in culture", Lasers in Surgery and Medicine, vol. 39, No. 4, pp. 373-378, year 2007.
Barushka et al., "Effect of Low-Energy Laser (He-Ne) Irradiation on the Process of Bone Repair in the Rat Tibia", Bone, vol. 16, No. I, pp. 47-55, Jan. 1995.
U.S. Appl. No. 13/264,755 Office Action dated Oct. 15, 2015.

\* cited by examiner

LOW LEVEL LASER THERAPY FOR ALZHEIMER'S DISEASE

CROSS-REFERENCE TO RELATED APPLICATION

This application claims the benefit of U.S. Provisional Patent Application 61/468,017, filed Mar. 27, 2011, which is incorporated herein by reference.

FIELD OF THE INVENTION

This invention relates to the controlled application of therapeutic light energy. More particularly, this invention relates to the therapeutic irradiation of marrow-containing bone using infrared light and energy of other wavelengths in subjects having or developing Alzheimer's Disease.

BACKGROUND OF THE INVENTION

The meanings of certain acronyms and abbreviations used herein are given in Table 1.

TABLE 1

| Acronyms and Abbreviations | |
|---|---|
| AD | Alzheimer's disease |
| ATP | adenosine tri-phosphate |
| BM | bone marrow |
| IR | infrared |
| LED | light-emitting diode |
| LLLT | low level laser therapy |
| MSC | mesenchymal stem cell |
| ORT | object recognition test |
| SEM | standard error of the mean |

The bone marrow is a complex tissue featuring several different types of primitive cells: hematopoietic stem cells, mesenchymal stem cells (MSCs), endothelial progenitor cells, side population cells, and multipotent adult progenitor cells. Like other stem cells, mesenchymal stem cells are capable of multilineage differentiation from a single cell and in vivo functional reconstitution of injured tissues. One of the properties of stem cells is their capacity to migrate after infusion to one or more appropriate microenvironments. Certain stem cells are able to exit their production site, circulating in the blood before reseeding in their target tissues. For mesenchymal stem cells, the nature of homing sites and circulation into peripheral blood is still under debate. However, mesenchymal stem cells have been found after infusion in multiple tissues, leading to the hypothesis that they can home, and that they adjust their differentiation pathways to diverse tissue microenvironments.

SUMMARY OF THE INVENTION

Low level laser therapy (LLLT) has been found to modulate various biological processes by photostimulatory effects. Mesenchymal stem cells (MSCs) isolated from bone marrow (BM) of laser treated and non-laser-treated mature rats were grown in cullture. $\beta$-amyloids that are over-expressed in the brain of Alzheimer's disease (AD) of experimental animals or humans were added to the medium. The extent of $\beta$-amyloid degradation by the MSCs was determined. It was found that the laser treated MSCs degraded the $\beta$-amyloids to a significant higher extent than the non laser treated MSCs. AD-mice were given multiple LLLT to BM commencing at 4 month of age until 6 month. Non-laser sham treated AD-mice served as control. It was found that in the laser treated AD-mice (that were laser treated to the BM) neurological tests (fear and cognitive tests) demonstrated a significant (p<0.05) better neurological performance compared to the non-treated AD mice. Furthermore concomitantly with the improved neurological performance tests, the $\beta$-amyloid density in the hippocampal region of the brain was significantly less (p<0.05) in the laser-treated mice as compared to control. It is concluded that LLLT to the BM of AD mice most probably activates macrophagic activity in certain cells in the BM (microglial-like cells) that consequently migrate from the BM to the circulating blood and enter the brain. They may cause there degradation of $\beta$-amyloids, and as a result, significant improvement in cognitive function of the brain in the AD-mice.

In embodiments of the present invention, bone marrow is irradiated in vivo in order to treat Alzheimer's disease. The irradiation may be performed by transcutaneous application or direct application (on the bone) of infrared laser radiation over the area of a marrow-containing bone. Alternatively, other radiation sources may be used, including both coherent and incoherent sources, at both IR and other wavelengths. Although transcutaneous irradiation has the advantage of being non-traumatic, the irradiation may alternatively be applied directly to the bone marrow using invasive techniques.

There is provided according to embodiments of the invention an apparatus for administration of phototherapy to a bone of a subject with biostimulatory radiation, the apparatus including a transparent output interface, which is configured to be brought into contact with a skin surface overlying the bone, and a source of coherent light, which is configured to emit the radiation through the output interface so as to irradiate marrow of the bone at a sufficient intensity to engender removal of $\beta$-amyloid from a brain of the subject when the source of coherent light avoids irradiating the brain.

According to an aspect of the apparatus, the coherent light has a wavelength between 630-910 nm.

According to yet another aspect of the apparatus, the coherent light has a wavelength between 790-830 nm.

According to an aspect of the apparatus, the source of coherent light is a laser.

According to a further aspect of the apparatus, the source of coherent light includes at least one Gallium Aluminum Arsenide laser.

According to still another aspect of the apparatus, the source of coherent light is a light-emitting diode.

According to yet another aspect of the apparatus, the source of coherent light operates in a continuous wave mode of operation.

According to a further aspect of the apparatus, the source of coherent light operates in a pulsed mode of operation.

According to an aspect of the apparatus, the output interface has multiple openings including circumferentially oriented slots.

According to one aspect of the apparatus, the output interface s has multiple openings including longitudinally oriented slots.

According to an additional aspect of the apparatus, the source of coherent light includes multiple laser probes that emit the radiation to the marrow simultaneously.

According to still another aspect of the apparatus, the radiation has a wavelength of 804 nm at a power of 10-14 mW/cm2 and an exposure duration of 100-120 seconds.

According to yet another aspect of the apparatus, a beam diameter of the radiation within the marrow is 0.3 cm.

There is further provided according to embodiments of the invention a method of phototherapy, which is carried out, responsively to a determination that Alzheimer's disease exists or is developing in a brain of a living subject, by irradiating marrow within a bone of the subject that is remote from the brain with biostimulatory radiation of sufficient intensity to engender β-amyloid degradation.

There is further provided according to embodiments of the invention a use of a coherent light source in producing a light irradiation apparatus, responsively to a determination that Alzheimer's disease exists or is developing in a brain of a living subject, to deliver biostimulatory radiation of sufficient intensity to engender β-amyloid degradation in the brain by irradiating marrow within a bone of the subject.

According to an aspect of the invention, the β-amyloid degradation includes phagocytosis by migrating mesenchymal stem cells that have experienced the radiation.

According to another aspect of the invention, irradiating is performed by delivering visible or infrared light energy to the marrow by positioning a probe including a source of coherent light on a body surface of the subject, and transcutaneously, or directly on the bone surface, directing the energy from the probe toward the marrow. The source of coherent light may be a laser or a light-emitting diode. Directing the energy from the probe may be performed in a continuous wave mode of operation or in a pulsed mode of operation.

According to a further aspect of the invention, irradiating is performed by delivering visible or infrared light energy to the marrow by positioning a laser probe beneath a body surface of the subject, and directing the energy from the probe toward the marrow.

According to an aspect of the invention, positioning the laser probe includes inserting a distal portion of the probe into a medullary cavity of the bone and irradiating is performed by directing light through multiple openings in the distal portion of the probe. The multiple openings may be circumferentially oriented slots or longitudinally oriented slots. The probe may also be transparent to the laser/light energy and emit the energy from its surface to the bone marrow tissue.

According to an additional aspect of the invention, irradiating includes positioning multiple laser probes on the subject and directing the radiation from the multiple laser probes to the marrow simultaneously. According to still another aspect of the invention, irradiating includes directing first and second ones of the multiple laser probes to a first bone and a second bone, respectively.

According to yet another aspect of the invention, the radiation has a wavelength of 804 nm at a power of 10-14 mW/cm$^2$ and an exposure duration of 100-120 seconds. According to a further aspect of the invention, a beam diameter of the radiation within the marrow is 0.3 cm.

According to still another aspect of the invention, irradiating is performed multiple times according to a cyclic dosage schedule. The cyclic dosage schedule may comprise six doses administered twice a week.

The bone may be a tibia, one or more bones of the pelvic girdle, an upper extremity, the upper limb girdle, ribs, skull, vertebrae, and sternum.

There is further provided according to embodiments of the invention a use of a coherent light source in producing a light irradiation apparatus responsively to a determination that Alzheimer's disease exists or is developing in a brain of a living subject to deliver biostimulatory radiation to marrow of a bone of the subject of sufficient intensity to stimulate mesenchymal stem cells therein to migrate from the bone.

DETAILED DESCRIPTION OF EMBODIMENTS

Figure 1:
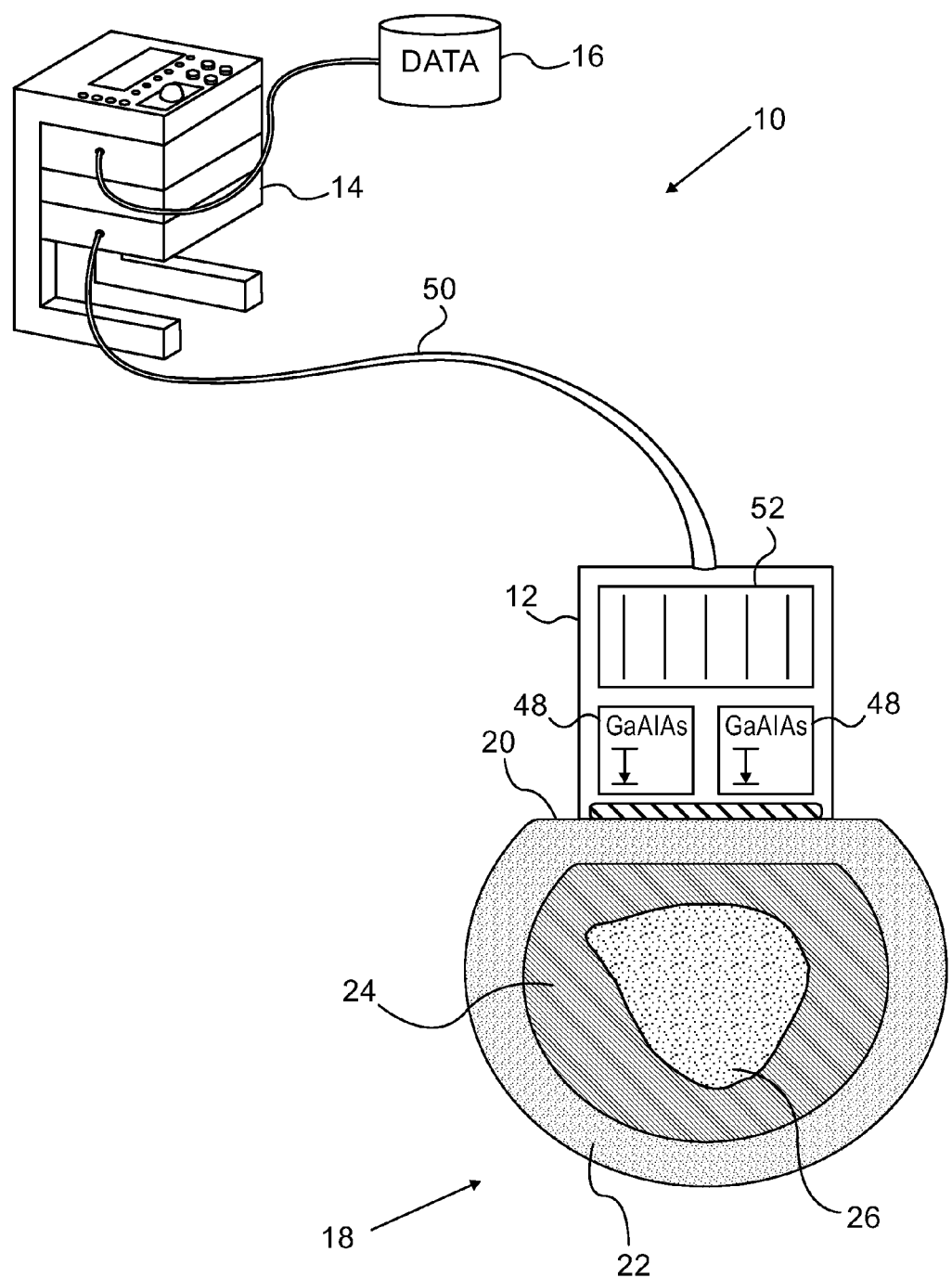
FIG. 1 is a pictorial diagram of a light irradiation system, which is constructed and operative in accordance with an embodiment of the invention.

In the following description, numerous specific details are set forth in order to provide a thorough understanding of the various principles of the present invention. It will be apparent to one skilled in the art, however, that not all these details are necessarily always needed for practicing the present invention. In this instance, well-known circuits, control logic, and the details of computer program instructions for conventional algorithms and processes have not been shown in detail in order not to obscure the general concepts unnecessarily.

Scientific background: Alzheimer's disease (AD) affects more than 18 million people worldwide and is characterized by progressive memory deficits, cognitive impairment, and personality changes. The main cause of AD is generally attributed to the increased production and accumulation of amyloid-beta (Aβ) proteins, in association with neurofibrillary tangle (NFT) formation that leads mainly to neuronal death in the hippocampus, which is critical for learning and memory (1). The presence of stem cells in the hippocampus has led to an increased interest in the phenomenon of adult neurogenesis and its role in hippocampal functioning (2). Many factors known to impact neurogenesis in the hippocampus are implicated in the pathogenesis of AD (2). Since neurogenesis is modifiable, stimulation of this process, or the potential use of stem cells, recruited endogenously or via transplantation, has been speculated as a possible treatment for neurodegenerative disorders and Alzheimer's disease. The bone marrow (BM) is an extremely complex organ with several different types of primitive cells: hematopoietic stem cells, mesenchymal stem cells (MSCs), endothelial progenitor cells, side population cells, and multipotent adult progenitor cells. Like other stem cells, MSCs are capable of multilineage differentiation from a single-cell and in-vivo functional reconstitution of injured tissues (3). One of the properties of stem cells is their capacity after infusion, to home in on the appropriate microenvironment(s) (4). While certain stem cells are able to exit their production site and circulate into the blood before reseeding in their target tissues, or MSCs, the homing sites and their circulation into peripheral blood is still debatable. However, MSCs have been found after infusion in multiple tissues, leading to the hypothesis that they can home in on, and adjust their differentiation pathway to, diverse tissue microenvironments (5). It was recently shown that intracerebral transplantation of bone-marrow-derived mesenchymal stem cells into the brain of an induced AD model reduced the Aβ protein levels and accelerated the activation of microglia cells when compared to sham-transplanted animals. Furthermore, it was suggested that blood-derived microglia (and not their resident counterparts in the brain) have the ability to eliminate amyloid deposits by a cell-specific phagocytic mechanism. These bone marrow-derived microglia cells are thus very efficient in restricting amyloid deposits (6). Therapeutic strategies aimed to improving their recruitment could potentially lead to a powerful new tool for the elimination of toxic senile plaques.

Low-level laser therapy (LLLT) has been found to modulate various biological processes (7, 8), such as increasing mitochondrial respiration and ATP synthesis (9), facilitating wound healing, and promoting the process of skeletal muscle regeneration and angiogenesis (10). It has been shown previously that laser irradiation induces synthesis of cell cycle regulatory proteins in satellite cells from skeletal muscles due to the activation of early cell cycle regulatory genes (11, 12). In an experimental model of the infarcted heart in rats and dogs, it was demonstrated that LLLT application at optimal power parameters to the heart significantly reduced infarct size (scar tissue formation) from 2 weeks and onward (13). This phenomenon was partially attributed to a 3- and 6-fold significant elevation in the number of undamaged mitochondria and ATP content, respectively, in the ischemic zone of the laser-irradiated rat hearts, as compared to non-irradiated rat hearts (14). Heat shock proteins, vascular endothelial growth factor, inducible NO synthase and angiogenesis were also elevated by LLLT over non-treated hearts (15). The precise mechanisms, associated with the effect of LLLT on cells and tissues are not yet clearly understood. There is evidence suggesting that a primary mitochondrial chromophore for photobiostimulation is cytochrome c oxidase. In addition to leading to increased ATP formation (16), photobiostimulation may also initiate secondary cell-signaling pathways. The effect of photobiostimulation on stem cells or progenitor cells has not been extensively studied. A remarkable increase in stem cell counts on the fourth day of regeneration was observed when the regeneration *Dugesia tigrina* (worms) was stimulated by laser irradiation (17). Laser application to normal human neural progenitor cells significantly increases ATP production in these cells (16). LLLT was found to significantly increase survival and/or proliferation of MSCs post-implantation into the ischemic/infarcted heart, followed by a marked reduction of scarring and enhanced angiogenesis (18).

In one embodiment of the invention, biostimulatory radiation is applied to the bone marrow responsively to an indication that Alzheimer's disease may exist or is developing within a living subject.

Turning now to the drawings, reference is initially made to FIG. 1, which is a pictorial diagram of a invention a coherent light source which is used for the production of a light irradiation apparatus light irradiation system 10, which is constructed and operative in accordance with an embodiment of the invention. The system 10 is suitable for administering radiant energy to the bone marrow follows A source of coherent light is linked to a control unit 14. The source may be a laser probe 12 as shown in FIG. 1. Alternatively, the other forms of coherent light may be used, e.g., solid state devices such as light-emitting diodes (LEDs). The laser probe 12 delivers low-level light output to a target tissue, details of which are presented below. The control unit 14 regulates the dosage of the light output as to intensity, duration, and time schedule. While the system 10 is shown in FIG. 1 as two separate components, this is exemplary. The control unit 14 and the laser probe 12 may be integral. For example the system 10 may be realized as a single, hand-held device. The laser may operate in a pulsed mode or a continuous wave mode of operation. An energy dose delivered in pulsed mode penetrates thick bones better and with less local heating than continuous wave mode for a given power output. Laser output devices described in U.S. Pat. No. 6,395,016 are suitable for the laser probe 12.

Optionally, the system 10 includes or is linked to a storage device 16 that holds data generated by the control unit 14. Such data may be used for research purposes, to aid treatment analysis, or to support business requirements of the therapeutic applications delivered by the system 10.

The target tissue is typically a marrow-containing bony structure. The example of FIG. 1 illustrates a transverse section through the shaft of tibia 18. The laser probe 12, shown facing the medial surface of tibia 18, is positioned against or proximate skin 20, soft tissues 22 and bony cortex 24, the target tissue being bone marrow tissue in medullary cavity 26. It is recommended, but not essential, to apply energy to bone marrow tissue having hematopoietic marrow, e.g., bones of the pelvic girdle or the sternum in adult subjects. When dealing with young children and middle aged humans, long bones such as the tibia may be chosen for convenience. The skin of the medial tibia is particularly advantageous as there is relatively little intervening soft tissue.

Figure 2:
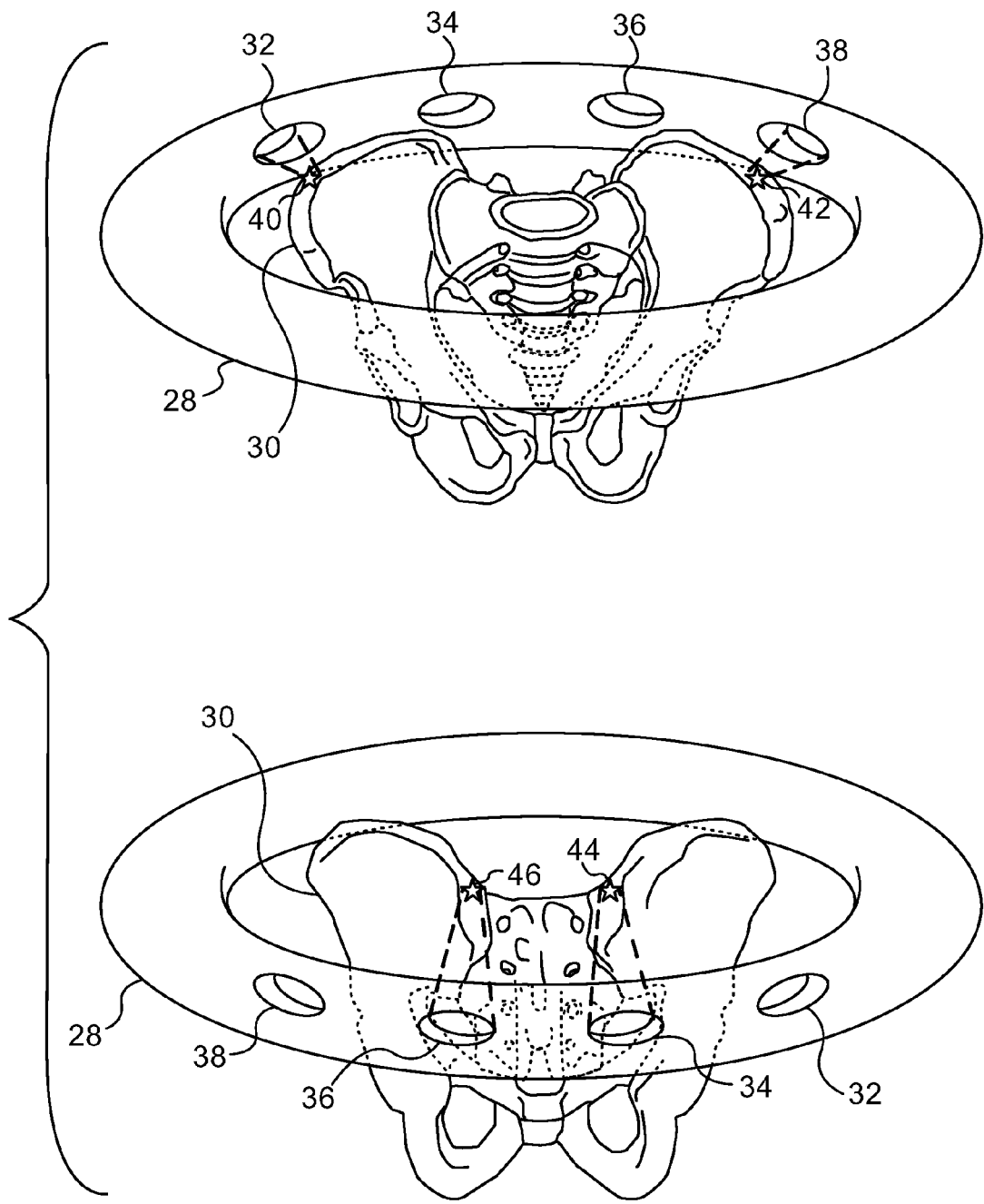
FIG. 2 illustrates an appliance for alignment of therapeutic laser output with desired locations in the human iliac bone.

Reference is now made to FIG. 2, which schematically illustrates an appliance 28 for alignment of therapeutic laser output with desired locations in the human iliac bone. The appliance 28 is shown assembled and superimposed on anterior and posterior views of an iliac bone 30 in the upper and lower portions of the figure, respectively. The appliance 28 can be realized as a mold made of silicon (or similar material) to be fitted around the pelvic girdle of a patient. Fixed openings or slots 32, 34, 36, 38 in the appliance 28 are adapted to receive respective laser probes (not shown) therein and direct the output energy to an intended target. While four slots are shown representatively in FIG. 2, the appliance 28 may have any number of slots. Laser light exiting slots 32, 38 may be directed to desired locations on the iliac bone 30, for example points 40, 42 on the anterior iliac crest, as best appreciated in the upper portion of FIG. 2. Laser probes in slots 34, 36 may be aimed at points 44, 46 on the posterior iliac crest as shown on the lower portion of FIG. 2.

Those skilled in the art can modify the appliance 28 for application of laser therapy to other bones, such as the ribs, vertebrae and sternum, all of which normally contain active bone marrow. LLLT may be applied beneficially to other marrow-containing bones, including the upper limb girdle, upper extremities and the skull. Indeed, the appliance 28 may be elaborated into a body vest suitable for laser application to many bones simultaneously.

The light application may be non-invasive, or invasive. In the latter case the geometry of the probe is adapted to insertion through a skin puncture or incision. Further alternatively, the light may be delivered via a probe or trephine that can penetrate the cortex 24 for application directly into the medullary cavity 26, using known light-handling techniques such as fiberoptics.

Reverting to FIG. 1, a light source may comprise one or more diode lasers 48 disposed in the laser probe 12. Alternatively, although not illustrated, the lasers may be disposed in the control unit 14. In the latter case, fiberoptic channels may be incorporated in cable 50 for delivery of the radiation through the probe. The lasers 48 are preferably configured to deliver light in the near infra-red spectrum. However, known sources of coherent light that emit in the visible spectrum may also be used.

Optionally, the laser probe 12 may be fluid-cooled in order to minimize discomfort and to avoid the possibility of burning the skin during application. For example, a heat radiator 52 may be provided. Other known air or liquid cooling techniques are also suitable.

The following considerations apply in the design of the light delivery system:

1. In embodiments employing fiberoptic delivery, the tip of each fiberoptic channel should have a relatively large diameter (1-8 cm) to avoid heating of the skin upon placement.

2. The laser probe 12 should insure "full contact" between the output interface of the probe and the skin. To this end the laser probe 12 may be constructed by adaptation of the teachings of U.S. Pat. No. 5,149,955 and U.S. Patent Application Publication No. 2010/0053391, which are herein incorporated by reference.

3. The apparatus should have the ability to deliver 50 mW to 7 W of optical power at the tip of the probe. For non-invasive applications, an output power level in excess of 1 W is desirable, in order to deliver an energy dose of sufficient intensity to engender tissue repair at a location in the body that is remote from the bone. Delivery of at least 10 mW/cm$^2$ to the bone marrow is needed for this purpose. Yet, 12-14 mW/cm$^2$ seems to have a beneficial effect at least as good as 10 mW/cm$^2$ When light is radiated directly into the medullary cavity 26, probes with energy levels at the lower end of the range are sufficient. Typically, the radiation has a wave-length of 804 nm at a power of 10-14 mW/cm$^2$ and an exposure duration of 100-120 seconds, using a beam diameter within the marrow of 3-8 cm.

4. An emergency "shut off" button should be provided on the laser probe 12 or the control unit 14.

5. The lasers 48 may be GaAlAs lasers, for emission at wavelengths of about 790-830 nm. Other biostimulatory wavelengths between about 630-910 nm can also be used. The radiation output may be either continuous-wave or pulsed.

Alternate Embodiment 1

Figure 3:
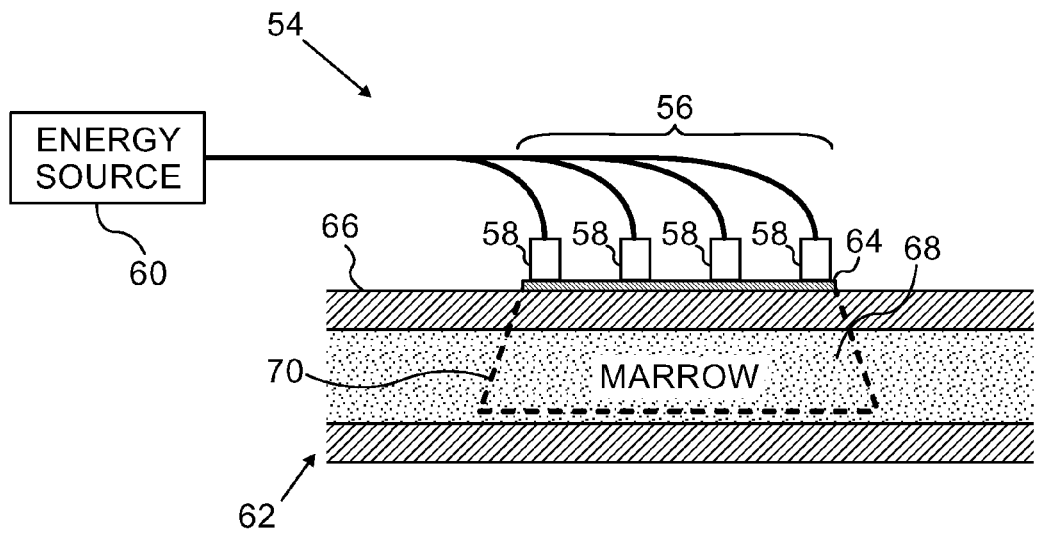
FIG. 3 is a pictorial illustration of a light irradiation system, which is constructed and operative in accordance with an alternate embodiment of the invention.

Reference is now made to FIG. 3, which is a schematic, pictorial illustration of a light irradiation system 54, which is constructed and operative in accordance with an alternate embodiment of the invention. In this embodiment a radiation delivery unit 56 comprises multiple laser probes 58. The delivery unit 56 is connected to a suitable energy source 60. The probes 58 are spaced apart on the body surface or on the surface of a marrow-containing bone 62. An optional mounting plate 64 for the probes 58 is shown in contact with periosteum overlying cortex 66. The plate 64 may be suitably fenestrated to accommodate the probes 58. Alternatively, the plate 64 may be and may be solid and transparent to light at the output wavelength of the probes 58. The plate 64 may be constructed using flexible materials in order to assure good contact between the probes 58 and irregular bone or body surfaces. As discussed above, a portion of the radiation emitted by the probes 58 penetrates into marrow cavity 68. In any case, advantages of the system 54 when compared with a single probe are increased flux of radiation delivered to a therapeutic radiation field 70 in the marrow cavity 68 and a more uniform distribution of radiation throughout the field 70.

Therapy may be administered using multiple instances of the delivery unit 56 simultaneously in the same or different body sites, for example one delivery unit 56 on each tibia. Many combinations involving different bones will occur to therapists skilled in the art.

Alternate Embodiment 2

Figure 4:
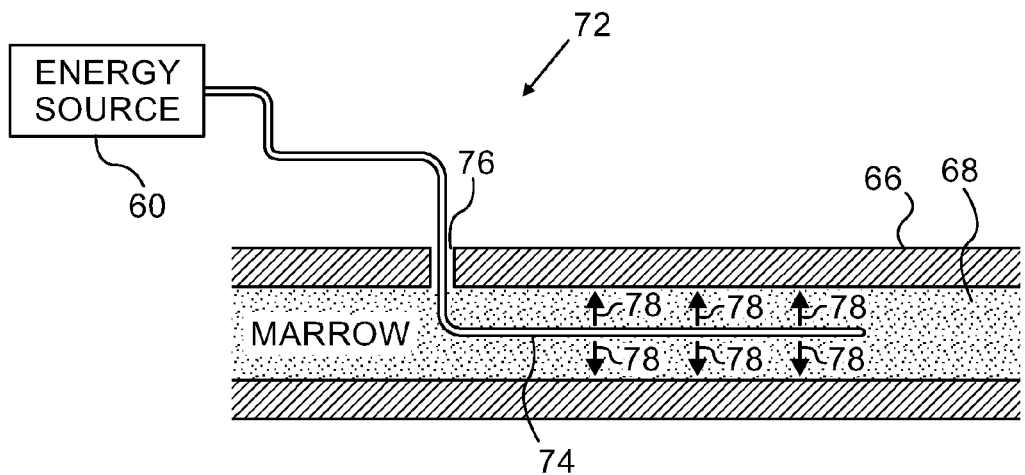
FIG. 4 is a schematic, pictorial illustration of an intramedullary light irradiation system, which is constructed and operative in accordance with an alternate embodiment of the invention.

Reference is now made to FIG. 4, which is a pictorial illustration of an intramedullary light irradiation system 72, which is constructed and operative in accordance with an alternate embodiment of the invention. A flexible fiberoptic probe 74 is inserted through a hole 76 that is drilled through the cortex 66 into the marrow cavity 68. The distal portion of the probe 74 is partially cladded using any suitable incomplete, cladding arrangement, for example having discrete openings, circumferential or longitudinal slots that enable radiation to escape radially, preferably in all directions from the probe 74 along the length of the distal portion, as represented by arrows 78. The multiple openings may occupy at least 50% of the area of the terminal 15 cm of the distal portion of the probe. The fiber can be incorporated in a modified version of the multi-lumen bone marrow aspiration that is taught in U.S. Pat. No. 6,849,051, which is herein incorporated by reference. 14. The output interface at the distal segment of the fiberoptic probe 74 may comprise fiberoptic elements that produce a light radiation directed radially to the long axis of the probe. The light radiation may be distributed about the entire circumference about the longitudinal axis so as to emit a 360 degree radiation pattern This embodiment has the advantage of delivering energy to the marrow more efficiently than the non-invasive embodiments described above, but carries the risk of infection, pain and other possible complications. As in the other embodiments, the power is adjusted to deliver a desired dose to the marrow cavity 68. The system 72 can operate at lower power than the non-invasive embodiments described above.

Experiment #1:

The aim of this experiment was to explore the ability of laser-treated MSCs to phagocytose Aβ proteins.

Isolation of MSCs was performed essentially as described previously (18). In brief, femur and tibia bones were excised from 10 (8-weeks-old) mice, and the bone marrow was collected using a stainless steel rod pushed through the marrow cavity. Cells were then seeded in 24-well culture plates at a concentration of 1.3×10$^6$ cell/cm$^2$ for one week (medium was changed 48 hrs post-seeding) as described previously (18). The Ga—Al—As laser (power output of 250 mw) was equipped with fiber optic. The power density on the cultured MSCs was set to 20 sec to yield 1.0 J/cm$^2$ energy density. Another set of 6-well plates containing MSCs were sham exposed (control) to the laser (cells treated as above, but the laser was not turned on). The laser-treated and the control MSCs were left for 3 days post laser-treatment and then incubated until 70% confluence.

Cells were then incubated with 0.12 µM HilyteFlour TM488-Aβ (1-42) for 2 hrs. Monocytes were labeled by addition of CD11b antibody to the cell suspension as previously described (19). The percentage of Aβ (1-42) phagocytosis was analyzed by FACS. A significant (p=0.041) 35% increase in phagocytosis of Aβ1-42 was found in the cells that were laser treated as compared to the non-laser-treated cells.

Figure 5:
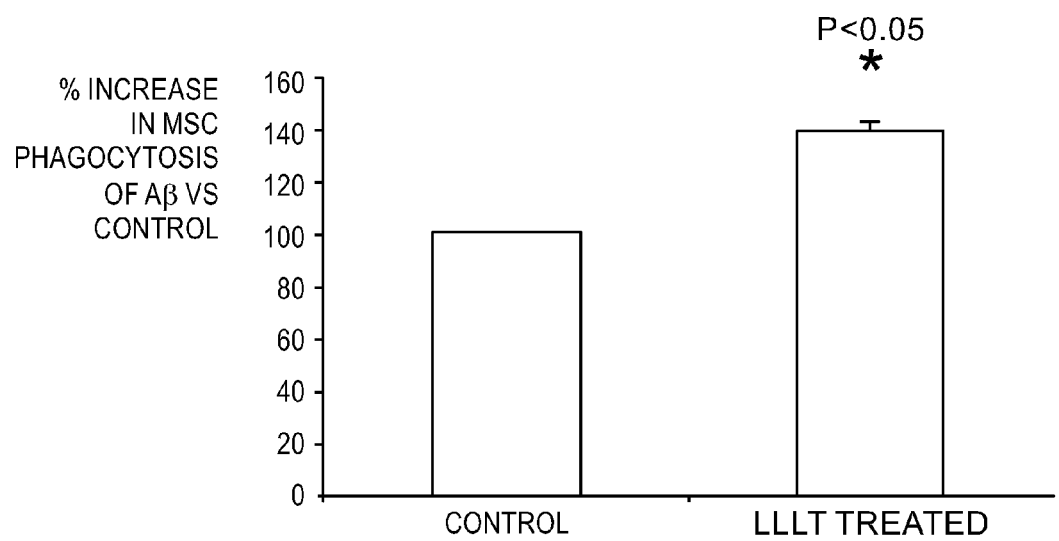
FIG. 5 is a bar graph illustrating the effect of LLLT on the ability of MSCs to induce phagocytosis in accordance with an embodiment of the invention.

Reference is now made to FIG. 5, which is a bar graph illustrating the effect of LLLT on the ability of MSCs (bone marrow derived monocytes) to induce phagocytosis of fluorescent Aβ beads. *p<0.05 in accordance with an embodiment of the invention.

It is concluded from Experiment #1 that laser application to the monocytes or other cells with macrophagic activity among the mesenchymal stem cell population in the bone marrow, causes a significant activation and/or proliferation of these cells and, hence, enhances their capacity to absorb specifically the Aβ proteins accumulated in the brain in AD mice.

Experiment #2.

The aim of this experiment was to investigate the therapeutic application of LLLT to BM in advanced stages of AD pathology. An AD mouse model obtained from Robert Vassar, USA, and bred at the facility of the Faculty of Life Sciences Tel-Aviv University was used. These amyloid precursor protein (APP) 5XFAD Tg mice, which display early plaque formation at 2 months of age, as well as impaired cognition, and also show neuronal death (CA1) and cerebral amyloid angiopathy at 7 months of age (20). A low-level laser, with a tunable power output of maximum of 400 mW was used. LLLT to the BM was performed by placing the distal tip of the fiberoptic directly on the middle portion of the medial part of the tibia after making a small incision in the skin. The beam diameter of the laser was 0.3 cm on the BM in the tibia. Irradiation power of the laser was set to 10 $mW/cm^2$ and exposure duration was 100 sec (comprising 1 $J/cm^2$). Control mice underwent the same procedure as the laser-irradiated group but the laser was not turned on. Control and laser-irradiated mice were chosen at random. Mice were treated with LLLT at 10 days intervals for two months starting at the age of four months (at this time the mice already have a well-established AD pathology). Mice were divided into three groups: Group I: (n=5) APP mice treated with LLLT every 10 days, commencing at 4 months of age. Group II: (n=5) Sham-operated APP mice that underwent the same procedure Group I but without the laser irradiation. Control and laser-irradiated rats were chosen at random. Group III: (n=5) intact wild-type (WT) mice of the same strain as the APP mice. At the age of 6 months the behavioral Object Recognition Test (ORT) was performed to determine visual recognition memory. In this test the more time the mouse spent around a new object relative to a recognized object (to which it had been exposed previously), the better its visual recognition capacity (cognitivity) and memory. In addition, well-defined hippocampus regions from the brain were selected for quantification of the Aβ present in them, using anti Aβ antibodies and histomorphometric software.

Figure 6:
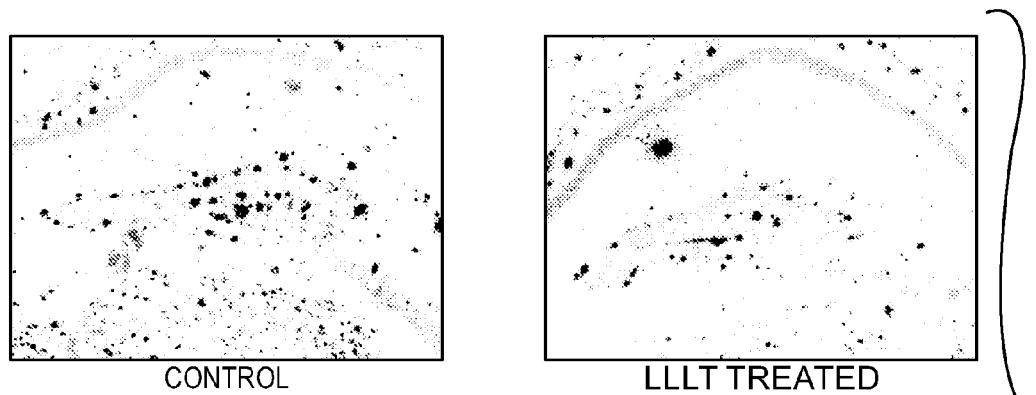
FIG. 6 is a composite illustration of a bar graph and representative fluorescent microscopy images showing the effect of LLLT to BM on amyloid burden in accordance with an embodiment of the invention.
Figure 6:
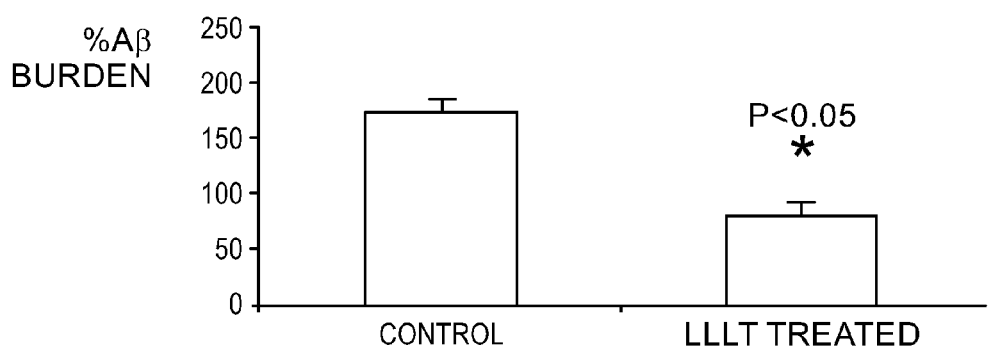

Reference is now made to FIG. 6, which is a composite illustration of a bar graph and representative fluorescent microscopy images showing the effect of LLLT to BM on amyloid burden in accordance with an embodiment of the invention. Four-month-old amyloid-β precursor protein (APP) 5XFAD Tg mice were treated with LLLT to their BM at 10-days intervals for 2 months. APP sham-operated (laser was not turned on) mice were used as control. Mice were sacrificed at the age of 6 months. Staining for total insoluble Aβ with anti-Aβ antibody in typical hippocampal microscopic sections of the brain was performed. Quantitative analysis of the Aβ burden in the sections was performed using histomorphological software. Results are expressed as mean±SEM of 5-7 mice in each group (p<0.05 represents the statistical significance). The images in the top portion of FIG. 6 are representative fluorescent microscopy images from the control and LLLT treated subjects. It is evident that the stainable Aβ in the image from the treated group is considerably less than in the image from the control group.

Figure 7:
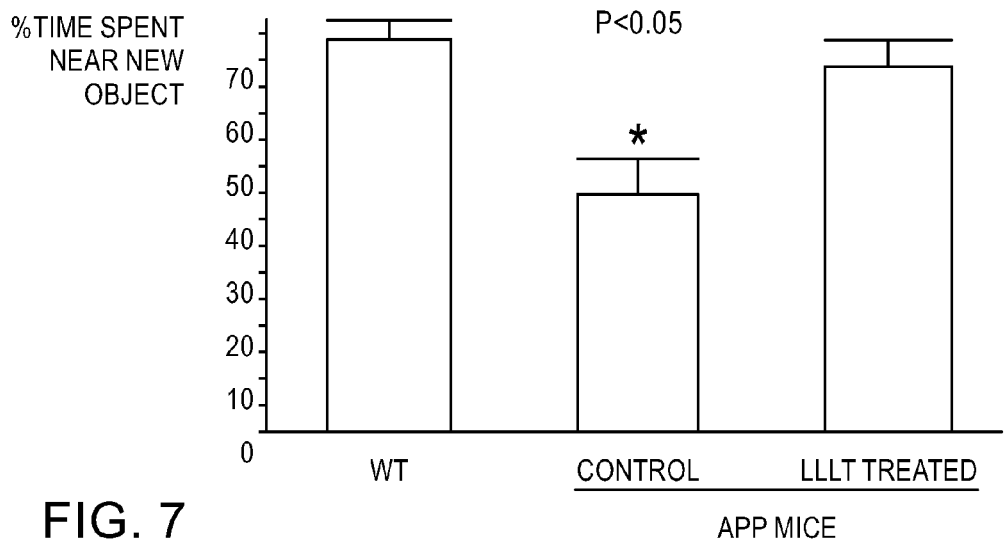
FIG. 7 is a bar graph showing the effect of LLLT to the BM on cognition in accordance with an embodiment of the invention.

It can be seen from inspection of FIG. 6 that the percentage of Aβ burden in the hippocampus region of the non-laser-treated mice was 180±15 (Mean±SEM) while in the laser-treated mice there was a significant (p<0.05) reduction of 68% in the Aβ burden relative to the non-treated mice. The results of the ORT (presented in FIG. 7) corroborate the above results. Wild-type-6-month-old mice (the same strain as the APP mice) demonstrated that the average percentage of time that the mice spent around a new object was 75±8%. This value was significantly (p<0.05) reduced to 48±11% in the group of 6-month-old, non-laser treated APP mice, indicating significant memory loss in the latter (FIG. 7). However, the multiple LLLT application to the BM of the APP mice caused almost complete recovery from this memory loss. The average percentage of time spent near a new object in the laser-treated mice was 68±8% seconds (FIG. 7). There was no statistical difference in the time spent near a new object between the wild-type (WT) mice and the APP mice that were treated by LLLT.

Reference is now made to FIG. 7, which is a bar graph showing the effect of LLLT to the BM on cognition of APP mice, as reflected in the object recognition test ORT, in accordance with an embodiment of the invention. Four-month-old amyloid-β precursor protein (APP) 5XFAD Tg mice were treated with LLLT to their BM or 10 days intervals for 2 months. The non-laser-treated group served as control. ORT was performed on all mice at the age of 6 months. The time spent around a new object as percentage of the total time spent around both the new and old object was significantly reduced in the APP mice as compared to wild-type, (non-transgenic) mice. Application of LLLT to the BM of APP mice significantly elevated this percentage of time to the level of the wild-type mice. Results are expressed as mean±SEM of 5-7 mice in each group (p<0.05).

Figure 8:
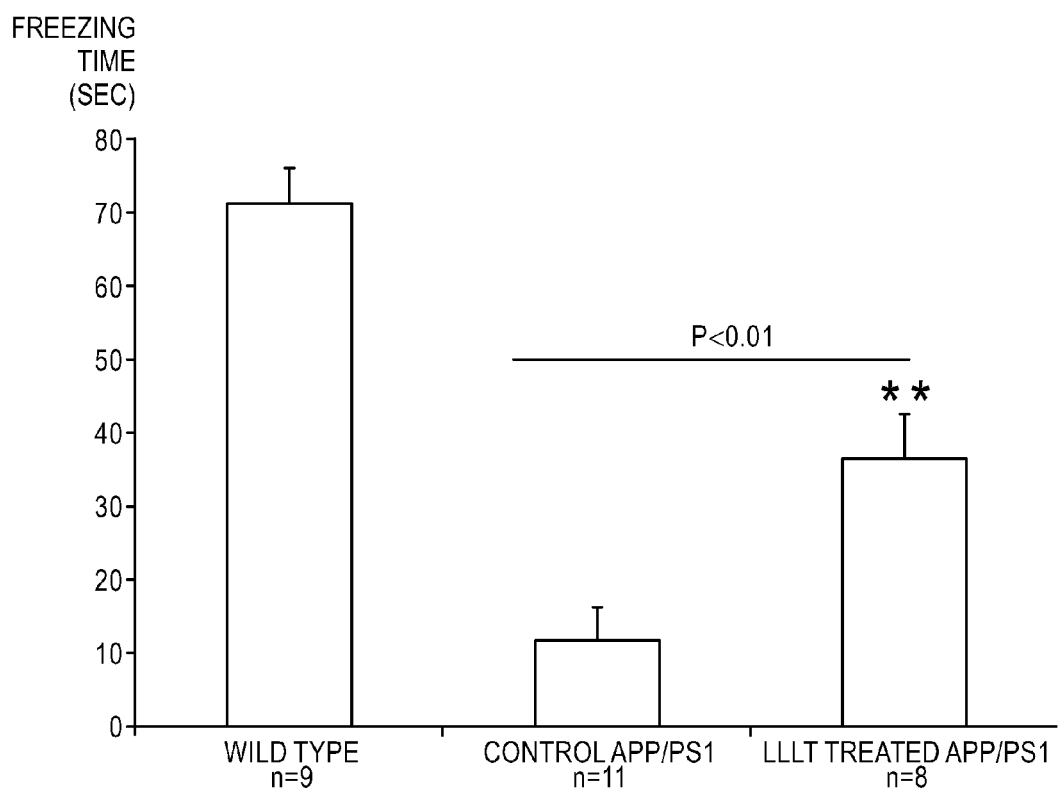
FIG. 8 is a bar graph showing the effect of LLLT to the BM of APP mice on their performance in the Fear test, in accordance with an embodiment of the invention.

Reference is now made to FIG. 8, which is a bar graph showing the Effect of LLLT to the BM of APP mice on their performance in the Fear test, in accordance with an embodiment of the invention. All other experimental procedures are as described above with reference to FIG. 7. In this test all mice are exposed to an electric shock on a metal grid open field platform in the first day. Twenty four hours after the electric shock each mouse is placed again on the same grid for a 4 min time interval. The time (in seconds) that each mouse is "freezing" in the same spot on the grid ("freezing time") rather than moving on the grid is recorded by a camera and uploaded into a computer. The higher the freezing time the better is the memory and cognitively of the mice. Note the significantly (p<0.0046) better performance of the LLLT (laser) AD-mice as compared to control non-treated AD mice. The results are mean±SEM of 11 control mice and 8 laser treated mice. (p<0.01). FIG. 8 presents the results of the Fear test of control (non-laser-treated), laser-treated mice, and wild-type mice. The results indicate that the freezing time was significantly (p<0.01) 3-fold higher (comprising 36±6 sec) in the non-laser-treated control mice than the laser treated mice where the freezing time was 12±5 sec. This indicates a significantly better cognitive and memory ability in the mice whose BM had been laser-treated as compared to non-treated mice Based on the results of this experiment as explained with reference to FIG. 5-FIG. 8, it appears that there was a significant elimination of Aβ in the brain of APP mice that were laser treated to the BM. From their better cognitive function (based on two neurobehavioral tests) it is concluded that LLLT to the BM has a profound beneficial effect on AD-mice even when treatment commences at an advanced stage with well-established memory loss and Aβ accumulation in the brain).

REFERENCES

1. Selkoe, D. J. Cell biology of protein misfolding: the examples of Alzheimer's and Parkinson's diseases. Nat Cell Biol 6:1054-1061. 2004.

2. Morgan, D. Amyloid, memory and neurogenesis. Exp Neurol 205:330-335. 2007.

3. Uccelli A, Moretta L, Pistoia V. Mesenchymal stem cells in health and disease. Nat Rev. Immunol. 8: 726-736. 2008.

4 Devine S M, Bartholomew A M, Mahmud N, Nelson M, Patil S, Hardy W, Sturgeon C, Hewett T, Chung T, Stock W, Sher D, Weissman S, Ferrer K, Mosca J, Deans R, Moseley A and Hoffman R. Mesenchymal stem cells are capable of homing to the bone marrow of non-human primates following systemic infusion. Exp Hematol 29:244-255. 2001.

5. Liechty K W, MacKenzie T C, Shaaban A F, Radu A, Moseley A M, Deans R, Marshak D R, Flake A W. Human mesenchymal stem cells engraft and demonstrate site-specific differentiation after in utero transplantation in sheep. Nat. Med. 6:1282-1286. 2000.

6. Simard A R, Soulet D, Gowing G, Julien J P, Rivest S. Bone Marrow-Derived microglia play a critical role in restricting senile plaque formation in Alzheimer's disease. Neuron 49:489-502.2006.

7. M J. Conlan, J W. Rapley and C M. Cobb. Biostimulation of wound healing by low energy laser irradiation. J Clin Periodontol 1996; 23:492-496. Review.

8. Karu, T. Ten lectures on basic science of laser phototherapy. Gragesberg Sweden. Prima Books. 2007.

9. A. Bibikova and U. Oron. Promotion of muscle regeneration in the toad (*Bufo viridis*) gastrocnemius muscle by low energy laser irradiation. Anat. Rec. 235:374-380. 1993.

10. Bibikova, A. Belkin and Oron U. Enhancement of angiogenesis in regenerating gastrocnemius muscle of the toad (*Bufo viridis*) by low energy laser irradiation. Ana.t Embryol. 190:597-602.1994.

11. Shefer G, Partridge T, Heslop L, Gross J.G, Oron U and Halevy O. Low-energy laser irradiation promotes the survival and cell cycle of skeletal muscle satellite cells. J. Cell Science. 115: 1461-1469. 2002

12. Shefer G, Oron U, Irintchev A, Wernig A and Halevy O. Skeletal muscle cell activation by low-energy laser irradiation: a role for the MEPK/ERK pathway. J Cell Physiol 187: 73-80. 2001.

13. Oron U, Yaakobi T, Oron A, Hayam G, Gepstein L, Rubin O, Wolf T and Ben Haim S. Attenuation of the formation of scar tissue in rats and dogs post myocardial infarction by low energy laser irradiation. Lasers Surg Med 28:204-211. 2001.

14. Oron U, Yaakobi T, Oron A, Mordechovitz D, Shofti R, Hayam G, Dror U, Gepstein L, Wolf T, Haudenschild C and Ben Haim S. Low energy laser irradiation reduces formation of scar tissue following myocardial infarction in dogs. Circulation 103:296-301. 2001.

15. Tuby H, Maltz L, Oron U. Modulations of VEGF and iNOS in the rat heart by low level laser therapy are associated with cardioprotection and enhanced angiogenesis. Lasers Surg Med 38:682-688. 2006.

16. Oron U, Ilic S, De Taboada L, and Streeter J. Ga—As (808 nm) laser irradiation enhance ATP production in human neuronal cells in culture. Photomed Laser Surg 25(3):180-182. 2007.

17. de Souza S C, Munin E, Alves L P, Salgado M A, and Pacheco M T. Low power laser radiation at 685 nm stimulates stem-cell proliferation rate in Dugesia tigrina during regeneration. J Photochem Photobiol B 80(3):203-207. 2005.

18. Tuby H, Maltz L and Oron U. Implantation of low-level laser irradiated mesenchymal stem cells into the infracted rat heart is associated with reduction in infarct size and enhanced angiogenesis. Photomed. Laser Surg. 27: 227-234.2009.

19. Farfara D, Trudler D, Segev-Amzaleg N, Galron R, Stein R, and Frenkel D., c-Secretase Component Presenilin Is Important for Microglia β-Amyloid Clearance. Ann. Neurol. 69:170-180. 2011

20. Oakley H, Cole SL, Logan S, Maus E, Shao P, Craft J, Guillozet-Bongaarts A, Ohno M, Disterhoft J, Van Eldik L, Berry R and Vassar R. Intraneuronal β-Amyloid Aggregates, Neurodegeneration, and Neuron Loss in Transgenic Mice with Five Familial Alzheimer's Disease Mutations: Potential Factors in Amyloid Plaque Formation. The J of Neuroscience. 26:10129-10140. 2006.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. An apparatus for administration of biostimulatory phototherapy radiation to a bone of a subject, the apparatus comprising:
   a transparent output interface,
   an appliance adapted to hold the output interface into contact with a skin surface overlying the bone or into contact with the bone; and
   a source of coherent light, which is configured to emit the radiation through the output interface so as to irradiate marrow of the bone at a sufficient intensity to improve brain function when the source of coherent light avoids irradiating a brain of the subject.

2. The apparatus according to claim 1, wherein the coherent light has a wavelength between 630-910 nm.

3. The apparatus according to claim 1, wherein the source of coherent light is configured to emit the radiation at an intensity sufficient to engender removal of β-amyloid from the brain of the subject.

4. The apparatus according to claim 1, wherein the source of coherent light is a laser.

5. The apparatus according to claim 1, wherein the output interface has multiple openings comprising circumferentially oriented or longitudinally oriented slots.

6. The apparatus according to claim 1, wherein the source of coherent light comprises multiple laser probes that emit the radiation to the marrow simultaneously.

7. The apparatus according to claim 1, wherein the output interface has an axis and a circumference about the axis, the output interface comprising fiberoptic elements produce a light radiation directed radially to the axis, the radiation being distributed about the entire circumference.

8. A method of phototherapy, comprising the step of:
   responsively to a determination that Alzheimer's disease exists or is developing in a brain of a living subject irradiating marrow within a bone of the subject that is remote from the brain with biostimulatory radiation of sufficient intensity to improve brain function while avoiding irradiating the brain of the subject.

9. The method according to claim 8, wherein irradiating comprises emitting the radiation at an intensity sufficient to engender removal of β-amyloid from the brain of the subject.

10. The method according claim 8, wherein removal of β-amyloid is mediated by mesenchymal stem cells that are stimulated by the radiation.

11. The method according to claim 8, wherein irradiating is performed by delivering visible or infrared light energy to the marrow by:
   positioning a probe comprising a source of coherent light on a body surface of the subject or directly on the bone; and
   directing the energy from the probe toward the marrow.

12. The method according to claim 11, wherein the source of coherent light is a laser.

13. The method according to claim 11, wherein the source of coherent light is a light-emitting diode.

14. The method according to claim 11, wherein directing the energy from the probe is performed in a continuous wave mode of operation.

15. The method according to claim 11, wherein directing the energy from the probe is performed in a pulsed mode of operation.

16. The method according to claim 8, wherein irradiating is performed by delivering visible or infrared light energy to the marrow by:
   positioning a laser probe beneath a body surface of the subject; and
   directing the energy from the laser probe toward the marrow.

17. The method according to claim 16, wherein positioning the laser probe comprises inserting a distal portion of the laser probe into a medullary cavity of the bone and irradiating is performed via directing light through multiple openings in the distal portion of the laser probe.

18. The method according to claim 17, wherein the multiple openings are circumferentially oriented slots on a fiberoptic element, the slots distributed so as to emit light via the fiberoptic element radially over 360 degrees about a longitudinal axis of the laser probe.

19. The method according to claim 17, wherein the multiple openings are longitudinally oriented slots.

20. The method according to claim 8, wherein irradiating comprises positioning multiple laser probes on the subject and directing the radiation from the multiple laser probes to the marrow simultaneously.

21. The method according to claim 8, wherein the bone comprises a plurality of bones, including at least a first bone and a second bone, wherein irradiating comprises directing first and second ones of the multiple laser probes to the first bone and the second bone, respectively.

22. The method according to claim 8, wherein the radiation has a wavelength of 804 nm at a power of 10-14 mW/cm$^2$ and an exposure duration of 100-120 seconds.

23. The method according to claim 8, wherein a beam diameter of the radiation within the marrow is from 3-8 cm.

24. The method according to claim 8, wherein irradiating is performed multiple times according to a cyclic dosage schedule.

25. The method according to claim 24, wherein the cyclic dosage schedule comprises six doses administered twice a week.

26. The method according to claim 8, wherein the bone is a tibia.

27. The method according to claim 8, wherein the bone comprises one or more bones of a pelvic girdle.

28. The method according to claim 8, wherein the bone comprises one or more bones of an upper extremity and upper limb girdle.

29. The method according to claim 8, wherein the bone comprises one or more of a rib, vertebra and sternum.

* * * * *